United States Patent
Kober et al.

[11] Patent Number: 6,087,305
[45] Date of Patent: Jul. 11, 2000

[54] MIXTURE CROP PROTECTION COMPOSITION COMPRISING THE MIXTURE AND ITS USE

[75] Inventors: Reiner Kober, Fussgoenheim; Karl-Heinrich Schneider, Kleinkarlbach; Wilhelm Rademacher, Limburgerhof; Reinhold Stadler, Kirrweiler; Bernd Burkhart, Mutterstadt; Guenter Oetter, Frankenthal; Matthias Gerber, Limburgerhof; Wessel Nuyken, Otterstadt; Oskar Schmidt, Schifferstadt; Hans Ziegler, Mutterstadt; Elmar Kibler, Hassloch; Thomas Kroehl, Mainz, all of Germany

[73] Assignee: BASF Aktiengesellschaft, Ludwigshafen, Germany

[21] Appl. No.: 08/795,666

[22] Filed: Feb. 6, 1997

[30] Foreign Application Priority Data

Feb. 6, 1996 [DE] Germany .................. 196 041 44

[51] Int. Cl.$^7$ ...................................... A01N 25/00
[52] U.S. Cl. .................. 504/313; 504/116; 504/189; 504/314; 424/504
[58] Field of Search .................. 504/116, 189, 504/313, 314, 220, 221, 115; 424/504

[56] References Cited

U.S. PATENT DOCUMENTS

| | | |
|---|---|---|
| 3,951,825 | 4/1976 | Carvor ..................................... 252/8.7 |
| 4,626,274 | 12/1986 | Hausmann et al. . |
| 4,834,908 | 5/1989 | Hazen et al. . |
| 5,554,576 | 9/1996 | Mookerjee et al. . |

FOREIGN PATENT DOCUMENTS

| | | |
|---|---|---|
| 2099631 | 1/1994 | Canada . |
| 0 579 052 | 1/1994 | European Pat. Off. . |
| 32 47 050 | 6/1984 | Germany . |
| 4-126875 | 4/1992 | Japan . |
| 4-348162 | 12/1992 | Japan . |
| WO 92/06596 | 4/1992 | WIPO . |
| WO 96/03872 | 2/1996 | WIPO . |

*Primary Examiner*—Deborah Carr
*Attorney, Agent, or Firm*—Oblon, Spivak, McClelland, Maier & Neustadt, P.C.

[57] ABSTRACT

A mixture consisting essentially of:

a) one or more dicarboxylic acid esters of the formula I $$ROOC—A—COOR \qquad (I)$$

in which the radicals R independently of one another are alkyl groups having 1 to 20 carbon atoms and A is alkylene having 1 to 20 carbon atoms, alkenylene or alkynylene each having 2 to 20 carbon atoms, cycloalkylidene or cycloalkenylidene each having 5 or 6 carbon atoms or phenylene and b) the product (II) of the reaction of a triglyceride based on carboxylic acids having 2 to 30 carbon atoms and ethylene oxide and/or propylene oxide in the presence of a base, which is useful for the production of crop protection compositions, for herbicidal crop protection compositions, and for controlling undesired plant growth, and spray mixtures comprising the compositions.

15 Claims, No Drawings

MIXTURE CROP PROTECTION COMPOSITION COMPRISING THE MIXTURE AND ITS USE

BACKGROUND OF THE INVENTION

1. Field of the Invention

The present invention relates to a mixture, comprising:
a) one or more dicarboxylic acid esters of the formula I

ROOC—A—COOR    (I)

where the radicals R independently of one another are alkyl groups having 1 to 20 carbon atoms and A is alkylene having 1 to 20 carbon atoms, alkenylene or alkynylene each having 2 to 20 carbon atoms, cycloalkylene or cycloalkenylene each having 5 or 6 carbon atoms or phenylene
and
b) the product (II) obtainable by the reaction of an oil or fat based on a triglyceride of carboxylic acids having 2 to 30 carbon atoms with ethylene oxide and/or propylene oxide in the presence of base.

The invention further relates to crop protection compositions which are conditioned in two parts and contain this mixture, the use of the mixture for their production and further the use of the crop protection compositions for controlling undesired plant growth, and spray mixtures suitable for this.

U.S. Pat. No. 4,834,908 discloses that the action of herbicidal crop protection active compounds can be increased by formulating them with a mixture of an ester of a long-chain carboxylic acid, a polyalkoxylated di- or trivalent inorganic acid and a long-chain carboxylic acid.

German Patent Application No. 32 47 050 describes the use of esters of natural fatty acids, e.g. dipropylene glycol pelargonate, as action-increasing formulation auxiliaries for herbicidal crop protection active compounds.

In International Publication No. WO 92/06596, it is explained in detail that the action of crop protection active compounds can be increased by means of a mixture of (i) a phosphoric acid alkylene oxide ester or a sulfonic acid, (ii) fatty acids or fatty acid esters or mixtures thereof and (iii) fatty acid polyalkylene glycol esters.

It can be seen from European Patent Application No. 0 579 052 that the action of crop treatment compositions can be improved if they are formulated with a mixture of a fatty alcohol ethoxylate and a dicarboxylic acid ester.

The above-mentioned formulation auxiliaries, however, may still not be satisfactory with respect to their increase in action in the case of crop protection active compounds, in particular when they are used as herbicides.

It is an object of the present invention to find formulation auxiliaries by means of which the application rates of crop protection active compounds and formulation auxiliaries can be lowered and/or the spectrum of action of the crop protection active compounds can be widened.

We have found that this object is achieved by the mixture defined at the outset, and its use for the preparation of pesticidal crop protection compositions and pesticidal crop protection compositions conditioned in two parts, which contain this mixture. In addition, we have found the use of the crop protection compositions for controlling undesired plant growth and the spray mixtures suitable for this purpose.

In the dicarboxylic acid esters of the general formula I

ROOC—A—COOR    (I)

the radicals R independently of one another are preferably unbranched or branched alkyl having 1 to 20 carbon atoms, such as methyl, ethyl, n-propyl, iso-propyl, n-butyl, 3-methylpropyl, 2-methylpropyl, 1,1-dimethylethyl, n-pentyl, n-hexyl, n-heptyl, n-octyl, n-nonyl, n-tridecyl, iso-tridecyl and 2-ethylhexyl.

A is preferably:
  unbranched or branched alkylene having 1 to 10 carbon atoms such as methylene, ethylene, n-propylene, iso-propylene, n-butylene, 3-methylpropylene, 2-methylpropylene, 1,1-dimethylethylene, n-pentylene, n-hexylene, n-heptylene, n-octylene, especially n-butylene ($CH_2$—$CH_2$—$CH_2$—$CH_2$):
  unbranched alkenylene having 2 to 8 carbon atoms, in particular cis- and trans-ethenylene,
  unbranched alkynylene having 2 to 8 carbon atoms, in particular ethynylene,
  cyclohexylene having 6 carbon atoms, in particular 1,2-cyclohexylene and 1,4-cyclohexylene or
  1,2-phenylene or 1,4-phenylene.

Mixture components I which are very particularly to be emphasized are the bis-iso-butyl-, bis-n-hexyl-, bis-2-ethylhexyl-, bis-n-nonyl- and bis-iso-tridecyl esters of unbranched dicarboxylic acids having 1 to 10 carbon atoms, especially those in which A is:
  1,2-cyclohexylene,
  1,4-cyclohexylene,
  $CH_2CH_2$,
  $CH_2CH_2CH_2$
  CH=CH (cis or trans) or in particular
  $CH_2CH_2CH_2CH_2$.

Bis(2-ethylhexyl) adipate is very particularly preferred as mixture component I.

Mixtures of the dicarboxylic acid esters I mentioned can also be used.

The dicarboxylic acid esters I are commercially available or can be prepared by methods known per se (cf. Houben-Weyl, Methoden der Organischen Chemie (Methods of Organic Chemistry), 4th Edition, Volume 8, page 522 et seq.).

The proportion of component I in the mixture is generally from 5 to 95, preferably from 25 to 93 and in particular from 60 to 80, % by weight.

The mixture component II is obtainable by the reaction of an oil/fat based on a triglyceride of carboxylic acids having 2 to 30 carbon atoms and ethylene oxide and/or propylene oxide in the presence of a base. Fatty acid alkoxylates are primarily formed.

In the triglycerides, three equivalents of carboxylic acid are esterified with glycerol. The carboxylic acids can be saturated or mono- or polyethylenically unsaturated.

Preferably, the present invention uses naturally occurring oils and fats which contain triglycerides as the main constituent. They can be crude, denatured or refined.

Suitable natural oils and fats are: vegetable oils such as olive oil, safflower oil, soybean oil, groundnut oil, cotton oil, corn oil, rape oil, castor oil, sunflower oil, coffee oil, linseed oil, coconut fat and mixtures thereof, animal fats and oils such as fish oils, e.g. sardine oil, herring oil, salmon oil, shark-liver oil or whale oil, and further tallow oil, bone oil, woolfat fractions and bovine tallow.

The following vegetable oils are preferred: castor oil, soybean oil, rape oil and corn oil. Particularly preferred of these is castor oil.

Per mol. of the triglyceride on which the oil is based, from 1 to 100, preferably from 10 to 35 and in particular from 15 to 30 mol. of ethylene oxide and/or propylene oxide are employed.

Suitable bases are especially inorganic bases such as the alkali metal or alkaline earth metal hydroxides, e.g. sodium hydroxide, potassium hydroxide or calcium hydroxide. Instead of the direct use of hydroxides, it is possible to use carbonates or hydrotalcites, which, if appropriate, were hydrophobized with aliphatic or aromatic carboxylic acids, alcohols having 4 to 22 carbon atoms or the ethoxylates of alcohols of this type, or basic alkaline earth metal phosphates such as strontium phosphate, barium phosphate and calcium phosphate, each of which also form hydroxide ions in the presence of small amounts of water.

The base particularly used is potassium hydroxide.

Per mol. of triglyceride, from 0.1 to 5, and in particular from 0.1 to 2, % by weight of base, based on the weight of the triglyceride, are generally added to the reaction mixture.

The reaction is generally carried out at elevated pressure, preferably at from 1 to 10 and in particular at from 1 to 5 bar and at from 80 to 230 and especially from 100 to 1500.

Working-up is in general carried out such that excess ethylene oxide or propylene oxide is removed under reduced pressure.

Otherwise, the carrying-out of such alkoxylation reactions and the isolation of the resulting reaction products is known to the person skilled in the art (cf. N. Schönfeldt, Grenzflächenaktive Ethylenoxidaddukte [Surface-active ethylene oxide adducts), Wissenschaftliche Verlagsgesellschaft mbH, Stuttgart, 1984).

The proportion of the component II in the mixture according to the invention is generally from 5 to 95, preferably from 7 to 50 and in particular from 20 to 40, % by weight. A preferred mixture is one comprising:

a) one or more dicarboxylic acid esters of the formula I

ROOC—A—COOR    (I)

where the radicals R independently of one another are alkyl groups having 1 to 20 carbon atoms and A is alkylene having 1 to 4 carbon atoms
and b) the product (II) obtainable by the reaction of an oil/fat based on a triglyceride of carboxylic acids having 10 to 20 carbon atoms and 10 to 30 mol. equivalents of ethylene oxide and/or propylene oxide in the presence of hydroxide ions.

The mixtures according to the invention generally exist as emulsion concentrates and have a high resistance to demixing.

A pesticidal crop protection active compound suitable for spray application or a formulation of the pesticidal crop protection active compound suitable for this form of application show an increased pesticidal action if they are mixed with the mixture according to the invention.

Pesticidal crop protection active compounds are specifically understood as meaning systemically acting insecticidal and fungicidal active compounds and growth regulators and, particularly preferably, herbicidal active compounds.

The herbicidal crop protection compositions contain one or more, for example, of the following herbicidal crop protection active compounds:

1,3,4-thiadiazoles such as buthidazole and cyprazole, amides such as allidochlor, benzoylpropethyl, bromobutide, chlorthiamide, dimepiperate, dimethenamid, diphenamid, etobenzanid, flamprop-methyl, fosamine, isoxaben, monalide, naptalame, pronamide, propanil, aminophosphoric acids such as bilanafos, buminafos, glufosinate-ammonium, glyphosate, sulfosate, aminotriazoles such as amitrole, anilides such as anilofos, mefenacet, aryloxyalkanoic acids such as 2,4-D, 2,4-DB, clomeprop, dichlorprop, dichlorprop-P, fenoprop, fluroxypyr, MCPA, MCPB, mecoprop, mecoprop-P, napropamide, napropanilide, triclopyr, benzoic acids such as chloramben, dicamba, benzothiadiazinones such as bentazone, bleachers such as clomazone, diflufenican, fluorochloridone, flupoxam, fluridone, pyrazolate, sulcotrione, carbamates such as carbetamid, chlorbufam, chlorpropham, desmedipham, phenmedipham, vernolate, quinolinic acids such as quinclorac, quinmerac, dichloropropionic acids such as dalapon, dihydrobenzofurans such as ethofumesate, dihydrofuran-3-ones such as flurtamone, dinitroanilines such as benefin, butralin, dinitramine, ethalfluralin, fluchloralin, isopropalin, nitralin, oryzalin, pendimethalin, prodiamine, profluralin, trifluralin, dinitrophenols such as bromofenoxim, dinoseb, dinoseb acetate, dinoterb, DNOC, minoterb acetate, diphenyl ethers such as acifluorfen-sodium, aclonifen, bifenox, chlornitrofen, difenoxuron, ethoxyfen, fluorodifen, fluoroglycofen-ethyl, fomesafen, furyloxyfen, lactofen, nitrofen, nitrofluorfen, oxyfluorfen, dipyridyls such as cyperquat, difenzoquat methyl sulfate, diquat, paraquat dichloride, imidazoles such as isocarbamid, imidazolinones such as imazamethapyr, imazapyr, imazaquin, imazethabenz-methyl, imazethapyr, oxadiazoles such as methazole, oxadiargyl, oxadiazon, oxiranes such as tridiphane, phenols such as bromoxynil, ioxynil, phenoxyphenoxypropionic acid esters such as clodinafop, cyhalofop-butyl, diclofop-methyl, fenoxaprop-ethyl, fenoxaprop-p-ethyl, fenthiapropethyl, fluazifop-butyl, fluazifop-p-butyl, haloxyfop-ethoxyethyl, haloxyfop-methyl, haloxyfop-p-methyl, isoxapyrifop, propaquizafop, quizalofop-ethyl, quizalofop-p-ethyl, quizalofop-tefuryl, phenylacetic acids such as chlorfenac, phenylpropionic acids such as chlorophenoxyprop-methyl, ppi active compounds such as benzofenap, flumiclorac-pentyl, flumioxazin, flumipropyn, flupropacil, pyrazoxyfen, sulfentrazone, thidiazimin, pyrazoles such as nipyraclofen, pyridazines such as chloridazon, maleic hydrazide, norflurazon, pyridate, pyridinecarboxylic acids such as clopyralid, dithiopyr, picloram, thiazopyr, pyrimidyl ethers such as pyrithiobac acid, pyrithiobac-sodium, KIH-2023, KIH-6127, sulfonamides such as flumetsulam, metosulam, triazolecarboxamides such as triazofenamid, uracils such as bromacil, lenacil, terbacil, and further benazolin, benfuresate, bensulide, benzofluor, butamifos, cafenstrole, chlorthal-dimethyl, cinmethylin, dichlobenil, endothall, fluorbentranil, mefluidide, perfluidone, piperophos.

Preferred herbicidal crop protection active compounds are those of the sulfonylurea type such as amidosulfuron, azimsulfuron, bensulfuron-methyl, chlorimuron-ethyl, chlorsulfuron, cinosulfuron, cyclosulfamuron, ethametsulfuron-methyl, flazasulfuron, halosulfuron-methyl, imazosulfuron, metsulfuron-methyl, nicosulfuron, primisulfuron, prosulfuron, pyrazosulfuron-ethyl, rimsulfuron, sulfometuron-methyl, thifensulfuron-methyl, triasulfuron, tribenuron-methyl, triflusulfuron-methyl.

Furthermore, preferred herbicidal crop protection active compounds are those of the cyclohexenone type such as alloxydim, clethodim, cloproxydim, cycloxydim, sethoxydim and tralkoxydim.

Very particularly preferred herbicidal active compounds of the cyclohexenone type are: tepraloxydim (cf. AGROW, No. 243, Mar. 11, 1995, page 21, caloxydim) and 2-(1-[2-{4-chlorophenoxy}propyloxyimino]-butyl)-3-hydroxy-5-(2H-tetrahydrothiopyran-3-yl)-2-cyclohexen-1-one and of the sulfonylurea type:

N-(((4-methoxy-6-[trifluoromethyl]-1,3,5-triazin-2-yl)amino)carbonyl)-2-(trifluoromethyl)benzenesulfonamide.

The fungicidal compositions contain one or more, for example, of the following fungicidal active compounds: sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc N,N-ethylene-bisdithiocarbamate, ammonia complex of zinc N,N'-propylene-bisdithiocarbamate, zinc N,N'-propylenebisdithiocarbamate, N,N'polypropylenebis(thiocarbamoyl) disulfide;

nitro derivatives, such as dinitro-(l-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)-phosphinyl]-3-phenyl-1,2,4-triazole, 2,3-dicyano-1,4-dithioanthraquinone, 2-thio-1,3-dithiolo[4,5-b]quinoxaline, methyl 1-butylcarbamoyl-2-benzimidazolecarbamate, 2-methoxycarbonylaminobenzimidazole, 2-(fur-2-yl)benzimidazole, 2-(thiazol-4-yl)benzimidazole, N-(1,1,2,2-tetrachloroethylthio)tetrahydrophthalimide, N-trichloromethyltetrahydrophthalimide, N-trichloromethylthiophthalimide, N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethylfuran-3-carboxylic acid cyclohexylamide, N-cyclohexyl-N-methoxy- 2,5-dimethylfuran-3-carboxamide, 2-methylbenzanilide, 2-iodobenzanilide, N-formyl-N-morpholine-2,2,2-trichloroethyl acetal, piperazine-1,4-diylbis(l-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2,(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichloro-phenoxyethyl)-NI-imidazolylurea, 1-(4-chlorophenoxy)-3,3-dimethyl-1-(1H-1,2,4-triazol-1-yl)-2-butanone, 1-(4-chloro-phenoxy)-3,3-dimethyl-l-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chloro-phenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino[α-(o-tolyloxy)-o-tolyl]acetate, methyl E-2-{2-[6-(2-cyanophenoxy)pyrimidin-4-yloxy]phenyl}-3-methoxyacrylate, methyl E-methoxyimino[α-(2-phenoxyphenyl)]acetamide, methyl E-methoxyimino[a-(2,5-dimethylphenoxy)-o-tolyl]acetamide, anilinopyrimidines such as N-(4,6-dimethylpyrimidine-2-yl)aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)pyrrol-3-carbonitrile, cinnamides such as 3-(4-chlorophenyl)-3-(3,4-dimethoxyphenyl)acrylic acid morpholide, and also various fungicides, such as dodecylguanidine acetate, 3-[3-(3,5-dimethyl-2-oxycyclohexyl)-2-hydroxyethyl]glutarimide, hexachlorobenzene, D,L-methyl N-(2,6-dimethylphenyl)-N-fur-2-oylalaninate, D,L-N-(2,6-dimethylphenyl)-N-(2'-methoxyacetyl)alanine methyl ester, N-(2,6-dimethylphenyl)-N-chloroacetyl-D,L-2-aminobutyrolactone, D,L-N-(2,6-dimethylphenyl)-N-phenylacetylalanine methyl ester, 5-methyl-5-vinyl-3-(3,5-dichlorophenyl)2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylamino-carbonyl-2-methoxyimino]acetamide, 1-[2-(2,4-dichlorophenyl)-pentyl]-1H-1,2,4-triazole, 2,4-difluoro-α-(1H-1,2,4-triazolyl-1-methyl) benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

The pesticidal crop protection active compounds can be employed as such or can already be formulated with known auxiliaries, the condition for these formulated products being that they are already suitable per se or after addition of the mixture according to the invention for spray application for controlling undesirable plant growth and for controlling pests such as insects and fungi.

The compositions according to the invention generally comprise from 5 to 50% by weight of one or more pesticidal crop protection active compounds.

The mixtures according to the invention can moreover additionally contain further customary additives such as surfactants, antifoams, co-solvents, etc.

Suitable surfactants are:

anionic surfactants, e.g. alkali metal, alkaline earth metal or ammonium salts of the fatty acids such as potassium stearate, alkylsulfates, alkyl ether sulfates, alkyl- or isoalkylsulfonates, alkylbenzenesulfonates such as Na dodecylbenzenesulfonates, alkylnaphthalenesulfonates, alkylmethyl ester sulfonates, acylglutamates, alkylsuccinic acid ester sulfonates, sarcosinates such as sodium lauroyl sarcosinate or taurates, cationic surfactants, e.g. alkyltrimethylammonium halides or alkylsulfates, alkylpyridinium halides or dialkyldimethylammonium halides or alkylsulfates, nonionic surfactants, e.g. alkoxylated animal or vegetable fats and oils such as corn oil ethoxylates, castor oil ethoxylates, tallow fat ethoxylates, glycerol esters such as glycerol monostearate, fatty alcohol alkoxylates and oxoalcohol alkoxylates, fatty acid alkoxylates such as oleic acid ethoxylates, alkylphenyl alkoxylates such as isononylphenol ethoxylates, fatty amine alkoxylates, fatty acid amide alkoxylates, sugar surfactants such as sorbitan fatty acid esters (sorbitan monooleate, sorbitan tristearate), polyoxyethylenesorbitan fatty acid esters, alkyl polyglycosides, N-alkylgluconamides, alkylmethyl sulfoxides, alkyldimethylphosphine oxides such as tetradecyldimethylphosphine oxide, zwitterionic surfactants, e.g. sulfobetaines, carboxybetaines, alkyldimethylamine oxides such as tetradecyldimethylamine oxide, polymer surfactants, e.g. di-, tri- or multi-blockpolymers of the type $(AB)_x$, ABA and BAB such as polyethylene oxide-block-polypropylene oxide, polystyrene-block-polyethylene oxide, AB comb polymers such as polymethacrylate or polyacrylate comb-polyethylene oxide, perfluoro surfactants, silicone surfactants, phospholipids such as lecithin, amino acid surfactants such as N-lauroyl glutamate, surface-active homo- and copolymers such as polyvinylpyrrolidone, polyacrylic acid, polyvinyl alcohol, polyethylene oxide, maleic anhydride-isobutene copolymers, vinylpyrrolidone-vinyl acetate copolymers.

Preferably, the surfactant used is one or more homogeneous or mixed esters of phosphoric acid or diphosphoric acid with polyalkylene oxide ethers, the polyalkylene oxide ethers generally having only a single hydroxyl group (e.g. Klearfac®, manufacturer BASF Corp.).

Suitable polyalkylene oxide ethers are, for example, ethers of alkylphenols such as nonylphenol or of branched or unbranched aliphatic alcohols, for example having 6 to 30, preferably having 10 to 20, carbon atoms and in particular of fatty alcohols having 10 to 12 carbon atoms.

The monohydroxylated polyalkylene oxide ethers are generally known or accessible in a manner known per se, especially by alkoxylation of the corresponding alcohols. Preferred alkoxylating agents are ethylene oxide and propylene oxide, which can be reacted with a suitable phosphorus compound individually, in a mixture, in succession or alternately, by means of which alkoxylation products of differing composition, for example having block structures, can result.

The preparation of these phosphoric acid esters is generally known and is carried out, for example, by reaction of the corresponding monofunctional polyalkylene oxide ether with phosphoric acid, diphosphorus pentoxide, polyphosphoric acid or phosphorus oxytrichloride (cf. "Nonionic Surfactants", Martin Schick (Ed.), Marcel Dekker, New York, 1964, Chapter 11, pages 372–394).

The proportion of the surfactants can be from 0 to 30, preferably from 2 to 15, % by weight.

Suitable antifoams are aliphatic or aromatic monoalcohols having 4 to 14, preferably 6 to 10, carbon atoms, such as n-octanol or n-decanol or silicone surfactants.

The proportion of the antifoams in the mixture is normally from 0.5 to 15 and especially from 3 to 8% by weight.

Suitable co-solvents are mineral oils, naturally occurring oils such as rape oil, soybean oil and the methyl esters of carboxylic acids on which these oils are based, such as methyl oleate and rape oil methyl ester, fatty acid esters, especially with $C_1$–$C_4$-alkanols and organic solvents such as benzenes or naphthalenes substituted by straight-chain or branched alkyl groups (Shellsol 150®, Shellsol 200® and Solvessoo® brands).

The proportion of the co-solvents in the mixture can be from 1 to 60 and especially from 5 to 30% by weight. Furthermore, the mixture can contain from 0 to 15 and especially from 2 to 10% by weight of water.

Additionally, the mixture can contain one or more carboxylic acids having from 4 to 20, in particular from 6 to 18, carbon atoms such as oleic acid or 2-ethylhexanoic acid and/or one or more of the dicarboxylic acids on which the compounds I are based, e.g. adipic acid, sebacic acid or succinic acid.

The proportion of these (di)carboxylic acids in the mixture is from 0 to 30, preferably from 0 to 10, % by weight.

The preparation of the mixture can be carried out by methods known per se by mixing the respective components, if appropriate with heating.

The preparation of the mixture according to the invention as a "stand-alone" product is preferred, i.e. the delivery of the mixture and of the herbicidal crop protection active compound to the consumer preferably takes place in separate packages (in contrast to the "built-in" product). The consumer has the advantage here that he can freely meter the amount of the mixture according to the invention, based on the crop protection active compound, and that remaining amounts of the mixture can also be used elsewhere without problems.

The compositions are put onto the market advantageously treated in two parts, as a "double pack" or "combipack", one part comprising the mixture and the other part comprising one or more unformulated herbicidal crop protection active compounds or one or more herbicidal crop protection active compounds formulated in a manner known per se. The above-mentioned customary additives which, if appropriate, are moreover contained in the mixtures can alternatively be contained simultaneously in one of these two parts or in both parts.

Suitable containers for the components of the compositions are any containers customarily used in crop protection compositions, especially bottles, cans and bags manufactured from chemically resistant plastics. The use of water-soluble containers is particularly advantageous and, among these, especially of water-soluble film bags, in particular based on polyvinyl alcohol.

The crop protection compositions according to the invention are processed with water to give the finished spray mixture before their use by the user, generally the farmer, in a manner known per se. In particular, to do this the parts of the combipack are first mixed and the herbicidal composition thus obtained is then diluted with water to the desired concentration.

The sprayable mixtures normally contain from 0.0001 to 10, preferably from 0.001 to 1, and in particular from 0.01 to 0.5, % by weight, for example, of the herbicidal crop protection active compound and from 0.001 to 50, preferably from 0.01 to 5 and in particular from 0.1 to 0.5, % by weight of the mixture according to the invention.

If the herbicidal crop protection active compounds are used as such for the production of the compositions, they generally have a purity of from 90 to 100%, preferably from 95 to 100% (according to NMR spectrum).

The application of the spray mixtures can be carried out in a manner known per se, especially by spraying using finely dispersing nozzles, for example, using a mobile spraying machine. The equipment and working techniques furthermore customary for this purpose are known to the person skilled in the art.

The herbicidal compositions based on the mixtures according to the invention control plant growth on noncultivated areas very well, especially at high application rates. In crops such as wheat (*Triticum aestivum*), rice (*oryza sativa*), corn (*Azea mays*), soybeans (*Glycine max*) and cotton (*Gossypium hirsutum*), they act against broad-leaved weeds and grass weeds without noticeably damaging the crop plants. This effect occurs especially at low application rates.

Depending on the particular application method, the herbicidal compositions can additionally be employed in a further number of crop plants for eliminating undesired plants. Suitable crops are, for example, the following:

*Allium cepa, Ananas comosus, Arachis hypogaea, Asparagus officinalis, Beta vulgaris* sp. *altissima, Beta vulgaris* sp. *rapa*l *Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* sp., *Manihot esculenta, Medicago sativa, Musa* sp., *Nicotiana tabacum* (*N. rustica*), *Olea europaea, Phaseolus lunatus, Phaseolus vulgaris, Picea abies, Pinus* sp., *Pisum sativum, Prunus avium, Prunus persica, Pyrus communis, Ribes sylvestre, Ricinus communes, Saccharum officinarum, Secale cereale, Solanum tuberosum, Sorghum bicolor* (*s. vulgare*), *Theobroma cacao, Trifolium pratense, Triticum durum, Vicia faba, Vitis vinifera.*

Moreover, the compositions can also be used in crops which are tolerant to the action of herbicides as a result of breeding, including genetic methods.

Undesirable plants are, for example: barnyard grass (*Echinochloa crus-galli*), *Brachiaria plantaginea, Ischaemum rugosum, Leptochloa dubia*, redroot pigweed (*Amaranthus retroflexus*), common lamb's quarters (*Chenopodium album*), catchweed bedstraw (*Galium aparine*), black nightshade (*Solanum nigrum*), blackgrass (*Alopecurus myosuroides*), wild oat (*Avena fatua*), smooth brome (*Bromus inermis*), annual bluegrass (*Poa annua*), giant foxtail (*Setaria faberi*), (self-sown) soft wheat (*Triticum aestivum*), (self-sown) corn (*Zea mays*), large crabgrass (*Digitaria sanguinulis*), windgrass (*Apera spicaventi*).

The application of the herbicidal compositions can be carried out pre-emergence or post-emergence. If the active compounds are less tolerable to certain crop plants, application techniques can be used in which the herbicidal compositions are sprayed with the aid of the spray apparatus such that the leaves of the sensitive crop plants are not affected if possible, while the active compounds reach the leaves of undesirable plants growing under them or the uncovered soil surface (post-directed, lay-by).

Additionally, it may be of use to apply the compositions on their own or together with further crop protection compositions, for example with compositions for controlling pests or phytopathogenic fungi and bacteria. Further of interest is the admixture of mineral salt solutions, which can be employed for eliminating nutritional and trace element deficiencies. Nonphytotoxic oils and oil concentrates can also be added.

Depending on the control target, time of year, target plants and stage of growth, the application rates of the herbicidal active compound are 0.1–1500, preferably 1–500, g/ha of active a.s.

The mixture according to the invention also increases the rate and intensity with which the herbicidal crop protection active compounds are absorbed. Furthermore, the resistance to rain, i.e. the danger of the herbicidal crop protection active compound being washed off by rain shortly after treatment, is improved. Especially in the case of the herbicidal crop protection active compounds of the cyclohexenone type, which are known as sensitive to UV light, the mixture according to the invention, therefore, leads to an increase in efficiency: the herbicidal active compounds penetrate into the plants more rapidly and are then protected from degradation by UV light.

EXAMPLES

Example 1

Synthesis example

Ethoxylation of castor oil in the presence of potassium hydroxide 1 mol. of castor oil and 1% by weight, based on caster oil, of technical-grade potassium hydroxide (potassium hydroxide content: 44%) were dehydrated for one hour at 120° C. and 10 mbar. The residue was initially introduced into an autoclave, and the autoclave was flushed with nitrogen gas and heated to from 120 to 130° C. At this temperature, 1 mol. of ethylene oxide was metered in at a pressure of from 1 to 5 bar in the course of 2 to 3 hours, and the mixture was then allowed to react until a constant internal pressure was reached in the autoclave (about 3 hours). The mixture was cooled to 80° C., and the autoclave was flushed with nitrogen gas. The crude product was removed from the autoclave at this temperature and degassed at 20 mbar and 80° C. with stirring.

1.5 g of the surfactant thus prepared, 10 ml of bis(2-ethylhexyl) adipate and 150 ml of water were intensively mixed. The amount of time until a phase boundary was visible for the first time again was then meausured. Table 1 in addition shows the results of comparison experiments for the emulsification of bis(2-ethylhexyl) adipate with known emulsifiers.

TABLE 1

Stability of the emulsion of bis (2-ethylhexyl) adipate and the reaction product from Example I as an emulsifier in comparison to other emulsifiers (EO = mol. of ethylene oxide)

| Emulsifier | Phase separation discernible after . . . minutes |
|---|---|
| Reaction product from Example 1 | 25 |
| Alkylphenol ethoxylate ethoxylated with 8 EO | 2 |
| Alkylphenol ethoxylate ethoxylated with 10 EO | 0.5 |
| Calcium-dodecylbenzenesulfonate | 3 |
| $C_{13}$-oxoalcohol ethoxylated with 12 EO | 0.5 |

Example 2

Use example

The increase in the action of herbicidal crop protection active compounds due to the mixture according to the invention could be confirmed by experiments in a greenhouse and outdoors.

This effect is particularly clear in comparison with known auxiliaries suitable for this purpose if both the crop protection active compounds and the activity-increasing additives were employed in amounts such that the effects in the plants were in the linear dose-response range, thus at about 20–80% foliar damage in the plants to be controlled.

In particular in experiments in the greenhouse, it was important, to protect even small activity differences, that defined growth and treatment conditions were maintained.

In the greenhouse, the test plant seeds were sown separately using a peat-containing substrate and according to species in plastic pots of about 12 cm diameter.

In pre-emergence treatment, the active compounds suspended or emulsified in water were applied by means of finely dispersing nozzles directly after sowing. The containers were lightly watered to promote germination and growth, and they were then covered with transparent plastic hoods until the plants had taken root. This covering causes a uniform germination of the test plants if this has not been adversely affected by the active compounds.

For the purposes of post-emergence treatment, the test plants were first raised, depending on growth form, to a growth height of from 3 to 15 cm and then treated with the active compounds suspended or emulsified in water. For this, the test plants were either sown directly and grown in the same containers or they were first raised separately as seedlings and transplanted into the test containers a few days before treatment.

The plants were kept species-specifically at from 10 to 25 or from 20 to 35° C. The test period extended over 2 to 4 weeks. During this time, the plants were tended, and their reaction to the individual treatments was assessed.

The procedure was similar in experiments outdoors or under outdoor-like conditions. The crop plants and typical associated undesirable plant species were sown in parallel rows or transplanted out.

In some cases naturally occurring plant populations were also included in the investigations. In certain cases, plants were also cultivated in pots under outdoor-like conditions.

Assessment was carried out on a scale from 0 to 100. "100" here means no emergence of the plants or complete destruction of at least the above-ground parts and "0" means no damage or normal course of growth.

The plants used in the tests were made up of the following species (Table 2):

TABLE 2

| Botanical Name | Common Name |
| --- | --- |
| undesired plants | |
| Zea mays | (self-sown corn) |
| Apera spica-venti | windgrass |
| Digitaria sanguinalis | large crabgrass |

The herbicidal crop protection active compound tepraloxydim was used for the experiments.

200 g of tepraloxydim, 80 g of Lutensol® AP8 (BASF AG), 20 g of HOE 1984 (anionic emulsifier from Hoechst AG) were made up to 1 l with Solvesso® 200 to give the herbicidal composition A.

Composition A was applied at an application rate of 4 g or 8 g/ha of a.s. of aqueous spray liquor, contained in 750 l/ha. The auxiliary mixture I according to the invention and the auxiliary mixture V disclosed in European Patent Application No. 0 579 052 were added to the spray liquor such that 500 ml/ha were applied. The recipes of the auxiliary mixtures were:

I 29% of ethoxylated castor oil (see Synthesis Example 1) 68% of bis(2-ethylhexyl) adipate (Plastomol DOA, BASF AG) 3% water V 30% Lutensol TO 12 ($C_{13}$-oxoalcohol reacted with 12 mol. of ethylene oxide, BASF AG) 70% bis(2-ethylhexyl)adipate Young corn (self-sown corn), windgrass and large crabgrass plants were treated with the ready-to-use spray liquor (750 l/ha). After eight days, the following effects were found which confirm an efficiency-enhancing action of the auxiliary mixture according to the invention (see Table 3):

TABLE 3

| Application rates of herbicide (g/ha of a.s.) | Auxiliary mixture | | % plant damage for | | |
| --- | --- | --- | --- | --- | --- |
| | I (g/ha) | V (g/ha) | (Self-sown) corn | Windgrass | Large crabgrass |
| 4 | — | — | 0 | 25 | 75 |
| 4 | 125 | — | 50 | 75 | 85 |
| 4 | — | 125 | 45 | 75 | 85 |
| 4 | 1000 | — | 60 | 65 | 90 |
| 4 | — | 1000 | 40 | 60 | 85 |
| 8 | — | — | 20 | 30 | 80 |
| 8 | 125 | — | 60 | 70 | 95 |
| 8 | — | 125 | 45 | 65 | 90 |
| 8 | 1000 | — | 55 | 75 | 90 |
| 8 | — | 1000 | 50 | 60 | 90 |

What is claimed as new and desired to be secured by Letters Patent of the United States is:

1. A method of preparing a pesticidal crop protection composition, comprising:

mixing a mixture of a component (a) of at least one dicarboxylic acid ester of formula I

ROOC—A—COOR (I)

wherein the radicals R independently of one another are $C_{1-20}$-alkyl groups and A is $C_{1-20}$-alkylene, $C_{2-20}$-alkenylene, $C_{2-20}$-alkynylene, $C_{5-6}$-cycloalkylene, $C_{5-6}$-cycloalkenylene or phenylene; and a component (b) of a product (II) prepared by the reaction of an oil or fat based on at least one triglyceride of a carboxylic acid having 2–30 carbon atoms with ethylene oxide and/or propylene oxide in the presence of base; with components necessary to form said pesticidal crop protection composition.

2. The method of claim 1, wherein the at least one dicarboxylic acid ester of component (a) is bis(2-ethylhexyl) adipate.

3. The method of claim 1, wherein the oil of component (b) is castor oil, soybean oil, rape oil or corn oil.

4. A crop protection composition, conditioned in two parts:

one part comprising a mixture of a component (a) of at least one dicarboxylic acid ester of formula I

ROOC—A—COOR (I)

wherein the radicals R independently of one another are $C_{1-20}$-alkyl groups and A is $C_{1-20}$-alkylene, $C_{2-20}$-alkenylene, $C_{2-20}$-alkynylene, $C_{5-6}$-cycloalkylene, $C_{5-6}$-cycloalkenylene or phenylene; and a component (b) of a product (II) prepared by the reaction of an oil or fat based on at least one triglyceride of a carboxylic acid having 2–30 carbon atoms with ethylene oxide and/or propylene oxide in the presence of base; and the other part comprising at least one pesticidal crop protection active compound.

5. The two part crop protection composition of claim 4, wherein the at least one dicarboxylic acid ester of component (a) is bis(2-ethylhexyl) adipate.

6. The two part crop protection composition of claim 4, wherein the oil of component (b) is castor oil, soybean oil, rape oil or corn oil.

7. The two part crop protection composition of claim 4, wherein the pesticidal crop protection active compound contains a herbicidally active compound of the sulfonylurea type or of the cyclohexenone type.

8. The two part crop protection composition of claim 5, wherein the pesticidal crop protection active compound contains a herbicidally active compound of the sulfonylurea type or of the cyclohexenone type.

9. A method for controlling undesired plant growth, which comprises:

allowing a crop protection composition as claimed in claim 4 to act on crop plants, their habitat and/or their seed.

10. A method for controlling undesired plant growth, which comprises:

allowing a crop protection composition as claimed in claim 7 to act on crop plants, their habitat and/or their seed.

11. A method for controlling undesired plant growth, which comprises:

allowing a crop protection composition as claimed in claim 8 to act on crop plants, their habitat and/or seed.

12. A method of controlling undesired plant growth, comprising:

applying the crop protection composition as claimed in claim 4 to crop plant habitat.

13. A method of controlling undesired plant growth, comprising:

applying the crop protection composition as claimed in claim 5 to crop plant habitat.

14. A method of controlling undesired plant growth, comprising:

applying the crop protection composition as claimed in claim 7 to crop plant habitat.

15. An aqueous spray mixture, comprising:

a herbicidal crop protection active compound and a mixture of a component (a) of at least one dicarboxylic acid ester of formula I $$ROOC\text{—}A\text{—}COOR \qquad (I)$$

wherein the radicals R independently of one another are $C_{1-20}$-alkyl groups and A is $C_{1-20}$-alkylene, $C_{2-20}$-alkenylene, $C_{2-20}$-alkynylene, $C_{5-6}$-cycloalkylene, $C_{5-6}$-cycloalkenylene or phenylene; and a component (b) of a product (II) prepared by the reaction of an oil or fat based on at least one triglyceride of a carboxylic acid having 2–30 carbon atoms with ethylene oxide and/or propylene oxide in the presence of base.

* * * * *